(12) United States Patent
Ferrand et al.

(10) Patent No.: US 10,433,944 B2
(45) Date of Patent: Oct. 8, 2019

(54) PACKAGE FOR A SURGICAL MESH

(71) Applicant: Sofradim Production, Trévoux (FR)

(72) Inventors: Rebecca Ferrand, Cailloux sur Fontaines (FR); Thomas Vial, Villefranche sur Saone (FR); Barbara Grepinet, Reyrieux (FR)

(73) Assignee: Sofradim Production, Trevoux (FR)

( * ) Notice: Subject to any disclaimer, the term of this patent is extended or adjusted under 35 U.S.C. 154(b) by 218 days.

(21) Appl. No.: 15/131,116

(22) Filed: Apr. 18, 2016

(65) Prior Publication Data
US 2016/0310254 A1  Oct. 27, 2016

(30) Foreign Application Priority Data

Apr. 23, 2015  (EP) .................................... 15305621

(51) Int. Cl.
| | | |
|---|---|---|
| *A61B 17/06* | (2006.01) | |
| *A61L 15/00* | (2006.01) | |
| *A61F 2/00* | (2006.01) | |
| *A61L 2/20* | (2006.01) | |
| *B65D 6/08* | (2006.01) | |
| *B65D 6/34* | (2006.01) | |
| *A61L 2/26* | (2006.01) | |

(52) U.S. Cl.
CPC ............ *A61F 2/0095* (2013.01); *A61L 2/206* (2013.01); *A61L 2/26* (2013.01); *B65D 11/14* (2013.01); *B65D 11/22* (2013.01); *A61F 2/0063* (2013.01); *A61F 2230/0039* (2013.01); *A61L 2202/182* (2013.01)

(58) Field of Classification Search
CPC ............ A61F 2/0095; A61F 2230/0039; A61F 2/0063; A61L 2/206; A61L 2/26; A61L 2202/182; A61L 15/00; B65D 11/24; B65D 11/22; A61B 50/00; A61B 50/30; A61B 50/31
USPC .... 206/204, 210, 213.1, 223, 570, 571, 225, 206/440, 338, 438
See application file for complete search history.

(56) References Cited

U.S. PATENT DOCUMENTS

| 71,909 A | 12/1867 | Pierce |
|---|---|---|
| 188,668 A | 3/1877 | Pleukharp |
| 549,555 A | 11/1895 | White |

(Continued)

FOREIGN PATENT DOCUMENTS

| CA | 2925563 A1 * | 10/2016 | ............... B65B 7/02 |
|---|---|---|---|
| EP | 0 579 377 A2 | 1/1994 | |

(Continued)

OTHER PUBLICATIONS

European Search Report for EP15305621.3 date of completion is Oct. 7, 2015 (3 pages).

*Primary Examiner* — Rafael A Ortiz

(57) ABSTRACT

The package (1) for a surgical mesh (100) comprises:
a receiving member (2) configured and dimensioned to receive at least one surgical mesh (100), and
a covering member (3) configured and dimensioned to cover the said at least one surgical mesh (100) maintaining with the receiving member (2) the surgical mesh (100) in a substantially flat position, and
a gas channelling network interposed between the said receiving member (2) and the said covering member (3) configured to channel a sterilization gas within the at least one surgical mesh (100).

18 Claims, 6 Drawing Sheets

(56) References Cited

U.S. PATENT DOCUMENTS

| | | | |
|---|---|---|---|
| 709,392 A | 9/1902 | Brown | |
| 816,026 A | 3/1906 | Meier | |
| 3,166,072 A | 1/1965 | Sullivan, Jr. | |
| 3,221,746 A | 12/1965 | Noble | |
| 3,276,172 A | 10/1966 | Hjalmar | |
| 3,494,006 A | 2/1970 | Brumlik | |
| 3,897,713 A | 8/1975 | Gugle | |
| 4,015,504 A | 4/1977 | Rosan, Sr. et al. | |
| 4,114,624 A | 9/1978 | Haverstock | |
| 4,203,520 A | 5/1980 | Schuster | |
| 4,224,946 A | 9/1980 | Kaplan | |
| 4,259,959 A | 4/1981 | Walker | |
| 4,647,300 A | 3/1987 | Sheets | |
| 4,798,292 A * | 1/1989 | Hauze | A61L 2/26 206/439 |
| 5,026,385 A | 6/1991 | Schutte et al. | |
| 5,100,391 A | 3/1992 | Schutte et al. | |
| 5,209,755 A | 5/1993 | Abrahan et al. | |
| 5,342,376 A | 8/1994 | Ruff | |
| 5,403,346 A | 4/1995 | Loeser | |
| 5,403,347 A | 4/1995 | Roby et al. | |
| 5,405,000 A * | 4/1995 | Hagedon | B65D 81/075 206/216 |
| 5,470,340 A | 11/1995 | Bezwada et al. | |
| 5,502,092 A | 3/1996 | Barrows et al. | |
| 5,611,986 A | 3/1997 | Datta et al. | |
| 5,633,343 A | 5/1997 | Bezwada et al. | |
| 5,639,851 A | 6/1997 | Bezwada et al. | |
| 5,730,750 A | 3/1998 | Haradon | |
| 5,769,583 A | 6/1998 | Girbinger | |
| 5,797,936 A | 8/1998 | Kleihues | |
| 5,834,582 A | 11/1998 | Sinclair et al. | |
| 5,868,788 A | 2/1999 | Bezwada et al. | |
| 5,869,597 A | 2/1999 | Newman, Jr. et al. | |
| 5,951,997 A | 9/1999 | Bezwada et al. | |
| 5,954,723 A | 9/1999 | Spetzler | |
| 6,090,908 A | 7/2000 | Jamiolkowski et al. | |
| 6,102,919 A | 8/2000 | Licata | |
| 6,241,747 B1 | 6/2001 | Ruff | |
| 6,270,517 B1 | 8/2001 | Brotz | |
| 6,388,043 B1 | 5/2002 | Langer et al. | |
| 6,500,193 B1 | 12/2002 | Bezemer et al. | |
| 6,554,840 B2 | 4/2003 | Matsutani et al. | |
| 6,599,310 B2 | 7/2003 | Leung et al. | |
| 6,620,178 B1 | 9/2003 | Brotz | |
| 6,692,499 B2 | 2/2004 | Tormalaet et al. | |
| 6,794,484 B2 | 9/2004 | Newman, Jr. et al. | |
| 6,831,149 B2 | 12/2004 | Newman, Jr. et al. | |
| 6,848,152 B2 | 2/2005 | Genova et al. | |
| 6,889,839 B1 | 5/2005 | Rosten et al. | |
| 6,991,643 B2 | 1/2006 | Saadat | |
| 7,070,858 B2 | 7/2006 | Shalaby et al. | |
| 7,129,319 B2 | 10/2006 | Shalaby | |
| 7,225,512 B2 | 6/2007 | Genova et al. | |
| 7,276,073 B2 | 10/2007 | Adams | |
| 7,371,253 B2 | 5/2008 | Leung et al. | |
| 7,374,566 B1 | 5/2008 | Schossau | |
| 7,445,624 B2 | 11/2008 | Freier et al. | |
| 7,601,164 B2 | 10/2009 | Wu | |
| 7,624,487 B2 | 12/2009 | Trull et al. | |
| 7,806,908 B2 | 10/2010 | Ruff | |
| 7,913,365 B2 | 3/2011 | Genova et al. | |
| 7,959,641 B2 | 6/2011 | Sorensen et al. | |
| 7,967,841 B2 | 6/2011 | Yuan et al. | |
| 7,975,698 B2 | 7/2011 | Browning | |
| 7,996,967 B2 | 8/2011 | Genova et al. | |
| 7,996,968 B2 | 8/2011 | Genova et al. | |
| 8,011,072 B2 | 9/2011 | Genova et al. | |
| 8,015,678 B2 | 9/2011 | Genova et al. | |
| 8,020,263 B2 | 9/2011 | Genova et al. | |
| 8,028,387 B2 | 10/2011 | Genova et al. | |
| 8,028,388 B2 | 10/2011 | Genova et al. | |
| 8,032,996 B2 | 10/2011 | Trull et al. | |
| 8,083,770 B2 | 12/2011 | Ruff et al. | |
| 8,100,940 B2 | 1/2012 | Leung et al. | |
| 8,118,834 B1 | 2/2012 | Goraltchouk et al. | |
| 8,161,618 B2 | 4/2012 | Maiorino et al. | |
| 8,192,462 B2 | 6/2012 | Sulamanidze et al. | |
| 8,273,105 B2 | 9/2012 | Cohen et al. | |
| 8,551,137 B2 | 10/2013 | Cohen et al. | |
| 8,888,810 B2 | 11/2014 | Hadba et al. | |
| 9,011,133 B2 | 4/2015 | Marczyk et al. | |
| 2001/0021861 A1 | 9/2001 | Boebel et al. | |
| 2002/0185406 A1 * | 12/2002 | Massengale | A61M 5/002 206/571 |
| 2003/0032961 A1 | 2/2003 | Pelo et al. | |
| 2003/0041426 A1 | 3/2003 | Genova et al. | |
| 2003/0149447 A1 | 8/2003 | Morency et al. | |
| 2004/0010275 A1 | 1/2004 | Jacobs et al. | |
| 2004/0078046 A1 | 4/2004 | Barzell et al. | |
| 2004/0093028 A1 | 5/2004 | Ruff | |
| 2004/0226427 A1 | 11/2004 | Trull et al. | |
| 2004/0237736 A1 | 12/2004 | Genova et al. | |
| 2005/0065542 A1 | 3/2005 | Mansfield | |
| 2005/0161355 A1 * | 7/2005 | Matthis | A61C 19/02 206/370 |
| 2005/0267531 A1 | 12/2005 | Ruff et al. | |
| 2006/0095134 A1 | 5/2006 | Trieu et al. | |
| 2006/0241663 A1 | 10/2006 | Rice et al. | |
| 2007/0005109 A1 | 1/2007 | Popadiuk et al. | |
| 2007/0005110 A1 | 1/2007 | Collier et al. | |
| 2007/0038249 A1 | 2/2007 | Kolster | |
| 2007/0065663 A1 | 3/2007 | Trull et al. | |
| 2007/0074991 A1 | 4/2007 | Heisserer | |
| 2007/0187861 A1 | 8/2007 | Genova et al. | |
| 2007/0224237 A1 | 9/2007 | Hwang et al. | |
| 2007/0225761 A1 | 9/2007 | Shetty | |
| 2007/0257395 A1 | 11/2007 | Lindh et al. | |
| 2007/0289886 A1 * | 12/2007 | Cha | G11B 23/0306 206/308.1 |
| 2008/0082113 A1 | 4/2008 | Bishop et al. | |
| 2008/0109021 A1 | 5/2008 | Medoff | |
| 2008/0195147 A1 | 8/2008 | Stopek | |
| 2008/0221618 A1 | 9/2008 | Chen et al. | |
| 2008/0281357 A1 | 11/2008 | Sung et al. | |
| 2008/0312688 A1 | 12/2008 | Nawrocki et al. | |
| 2009/0076543 A1 | 3/2009 | Maiorino et al. | |
| 2009/0112259 A1 | 4/2009 | D'Agostino | |
| 2009/0140012 A1 | 6/2009 | Greer, Jr. et al. | |
| 2009/0143819 A1 | 6/2009 | D'Agostino | |
| 2009/0248066 A1 | 10/2009 | Wilkie | |
| 2009/0248070 A1 | 10/2009 | Kosa et al. | |
| 2009/0287245 A1 | 11/2009 | Ostrovsky et al. | |
| 2010/0016810 A1 | 1/2010 | Drews et al. | |
| 2010/0023055 A1 | 1/2010 | Rousseau | |
| 2010/0057123 A1 | 3/2010 | D'Agostino et al. | |
| 2010/0084780 A1 | 4/2010 | Lindh, Sr. et al. | |
| 2010/0146770 A1 | 6/2010 | Morency et al. | |
| 2010/0174299 A1 | 7/2010 | Viola et al. | |
| 2010/0230300 A1 | 9/2010 | Hunter et al. | |
| 2010/0275750 A1 | 11/2010 | Maiorino et al. | |
| 2010/0298871 A1 | 11/2010 | Ruff et al. | |
| 2010/0313729 A1 | 12/2010 | Genova et al. | |
| 2011/0022086 A1 | 1/2011 | D'Agostino et al. | |
| 2011/0046668 A1 | 2/2011 | Goraltchouk et al. | |
| 2011/0046669 A1 | 2/2011 | Goraltchouk et al. | |
| 2011/0125188 A1 | 5/2011 | Goraltchouk et al. | |
| 2011/0189355 A1 * | 8/2011 | Field | B65D 81/2069 426/129 |
| 2011/0190815 A1 | 8/2011 | Saliman | |
| 2011/0276090 A1 | 11/2011 | Berndt et al. | |
| 2011/0282384 A1 | 11/2011 | Odermatt et al. | |
| 2011/0282386 A1 | 11/2011 | Friedrich et al. | |
| 2011/0288583 A1 | 11/2011 | Goraltchouk et al. | |
| 2011/0288584 A1 | 11/2011 | Bojarski et al. | |
| 2011/0319932 A1 | 12/2011 | Avelar et al. | |
| 2012/0046675 A1 | 2/2012 | Bishop et al. | |
| 2012/0104644 A1 | 5/2012 | Lauria | |
| 2012/0118123 A1 | 5/2012 | Maiorino et al. | |

(56) References Cited

U.S. PATENT DOCUMENTS

2012/0132054 A1    5/2012  Maiorino et al.
2015/0021221 A1*  1/2015  Hendrickson .......... A61B 50/20
                                                               206/438

FOREIGN PATENT DOCUMENTS

| EP | 1075843 A1 | 2/2001 |
|---|---|---|
| EP | 2156795 A2 | 2/2010 |
| WO | 03/007839 A2 | 1/2003 |
| WO | 2004062459 A2 | 7/2004 |
| WO | WO 2005/073091 A2 | 8/2005 |
| WO | WO 2005/120395 A2 | 12/2005 |
| WO | WO 2007/047028 A1 | 4/2007 |
| WO | 2007131019 A2 | 11/2007 |
| WO | 2008042992 A2 | 4/2008 |
| WO | 2008112417 A2 | 9/2008 |
| WO | 2008141034 A1 | 11/2008 |
| WO | 2008157142 A2 | 12/2008 |
| WO | 2009105663 A2 | 8/2009 |
| WO | 2009/132284 A2 | 10/2009 |
| WO | 2009129251 A2 | 10/2009 |
| WO | 2009140012 A1 | 11/2009 |
| WO | WO 2013/184552 A1 | 12/2013 |

\* cited by examiner

PACKAGE FOR A SURGICAL MESH

CROSS-REFERENCE TO RELATED APPLICATIONS

This application claims benefit of and priority to European Patent Application Serial No. EP15305621.3 filed Apr. 23, 2015, the disclosure of the above-identified application is hereby incorporated by reference in its entirety.

TECHNICAL FIELD

The present invention relates generally to a package for a surgical mesh.

BACKGROUND OF THE RELATED ART

Surgical meshes used for wall reinforcement, for example for the abdominal wall, are widely used in surgery. These surgical meshes are intended to treat, for example, hernias by temporarily or permanently filling a tissue defect. These surgical meshes are made generally from a surgical biocompatible textile and can have a number of shapes, for example rectangular, circular or oval, depending on the anatomical structure to which they are to adapt. The surgical mesh is generally flat and may vary in dimensions, from for example 5×10 cm up to 30×50 cm, depending on the size of the defect to be treated.

Before being packaged as a commercial product and shipped to hospitals or end-users, the surgical mesh has to be sterilized to prevent contamination to the patient body in which it is intended to be implanted.

Gas sterilization is commonly used in the medical field and surgical meshes are usually sterilized by means of ethylene oxide (EtO) gas.

The sterilization process generally requires the immersion of the surgical mesh in ethylene oxide for a time sufficient for the gas to sterilize the surgical mesh. For handling purposes, the surgical mesh is usually inserted into a handling pouch before being submitted to the sterilization process.

The handling pouch is provided with a window made of a material which is impervious to contamination by microorganisms, bacteria and/or a biologically active substance which may come into contact with the pouch while it is being handled, while at the same time remaining permeable to a sterilization gas such as for example ethylene oxide. Such a material is for example a nonwoven made of filaments of a high density polyethylene bound together by heat and pressure, such as a product sold by the Du Pont de Nemours under the trademark "Tyvek®". The surgical mesh to be sterilized is therefore humidified by exposure to water vapor, inserted into a "Tyvek®" pouch and submitted to ethylene oxide gas for sterilization.

However, it may happen, in particular for large surgical meshes, that the ethylene oxide gas may not reach the entire surface of the surgical mesh and/or does not diffuse in the surgical mesh a sufficiently efficient manner when the surgical mesh is first packaged in a pouch with a "Tyvek®" window. This proves to be a problem as it is desirable that sterilization is completed to a high degree on the entire surface of the surgical mesh.

Furthermore, in order to proceed to ethylene oxide sterilization, the surgical mesh must be previously humidified. The larger the mesh, the more humid the mesh will be after the sterilization step. In addition, because of its intrinsic nature, the surgical mesh is subject to moisturization. Moisturization has to be avoided during transportation and storage so as to maintain optimal dry conditions of the surgical mesh at the moment of its use.

SUMMARY OF THE INVENTION

In this technical context, it would be desirable to provide a packaging for a surgical mesh allowing an efficient ethylene oxide gas sterilization of all surgical meshes, whatever their size, that would prevent humidity of ambient air to permeate through the packaging, and that would also favour drying of the surgical mesh during storage and transportation.

The present invention relates to a package for a surgical mesh comprising a receiving member configured and dimensioned to receive a surgical mesh, and a covering member configured and dimensioned to cover the said at least one surgical mesh maintaining with the receiving member the surgical mesh in a substantially flat position, and a gas channelling network interposed between the said receiving member and the said covering member configured to channel a sterilization gas within the surgical mesh.

Thus, the invention makes it possible to maintain a surgical mesh in a substantially flat position and to bring a sterilizing gas in the entire surface of the mesh. This proves to be a great advantage for large surgical meshes, which tend to be partially sterilised using prior art sterilizing techniques.

In a embodiment of the invention, the receiving member and the covering member define at least one gas diffusing compartment connected to the said gas channelling network.

In an embodiment of the invention, the covering member includes at least one cut off portion allowing a large exposure to a sterilizing gas and a large exposure for humidity absorption by a desiccant agent.

In an embodiment, the receiving member comprises a resting rib and an inner wall configured to receive the at least one surgical mesh and the covering member comprises at least one resting rib and an inner wall configured to maintain the at least one surgical mesh between the said resting ribs and to define the at least one gas diffusing compartment for a sterilizing gas.

In an embodiment, the receiving member comprises at least one groove and the covering member comprises at least one groove defining with at least one groove of the receiving member a channel for a sterilizing gas.

In an embodiment, the receiving member and/or the covering member comprise at least one transverse resting ribs forming at least two diffusing compartments.

In an embodiment, the receiving member and the covering member include peripheral rim provided with at least one locking pin and at least one corresponding locking opening.

In an embodiment, the peripheral rim includes a series of locking toothing.

In an embodiment, at least one of the receiving member and of the covering member includes a cavity configured to receive a capsule of desiccant material.

In an embodiment, the receiving member and the covering member have a substantially rectangular shape.

In an embodiment, the covering member includes at least two cut off portions.

In an embodiment, the covering member includes a central portion and two lateral portions extending from the central portion.

In an embodiment, the covering member includes a hinge allowing access to the surgical mesh.

In an embodiment, the hinge is formed by a weakened line.

In an embodiment, the hinge is positioned at the junction the central portion and the lateral portion.

BRIEF DESCRIPTION OF THE DRAWINGS

The foregoing objects and advantages of the present invention will become apparent from the reading of the following description in connection with the accompanying drawings, in which.

DETAILED DESCRIPTION

Reference will now be made to the drawings wherein like structures are provided with like reference designations.

Figure 1:
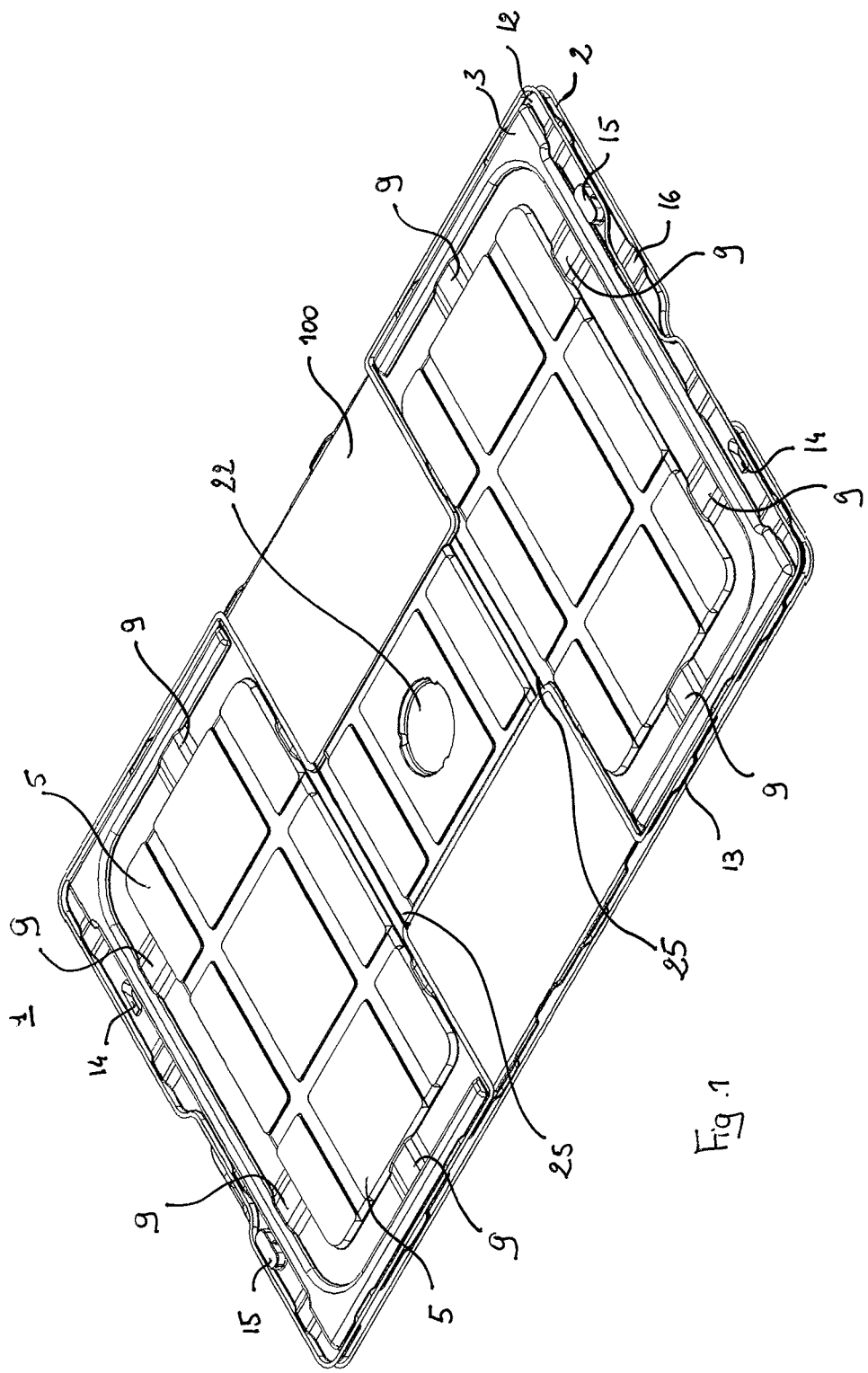
FIG. 1 includes a perspective view of a package according to an embodiment of the invention.

Turning to FIG. 1, a package 1 for a substantially rectangular mesh is shown in an perspective view.

Package 1 includes a receiving member 2 and a covering member 3. In the illustrated embodiment of FIG. 1, the package 1 is shown as rectangular; however, the package 1 may be of any suitable shape for receiving a surgical mesh.

Figure 3:
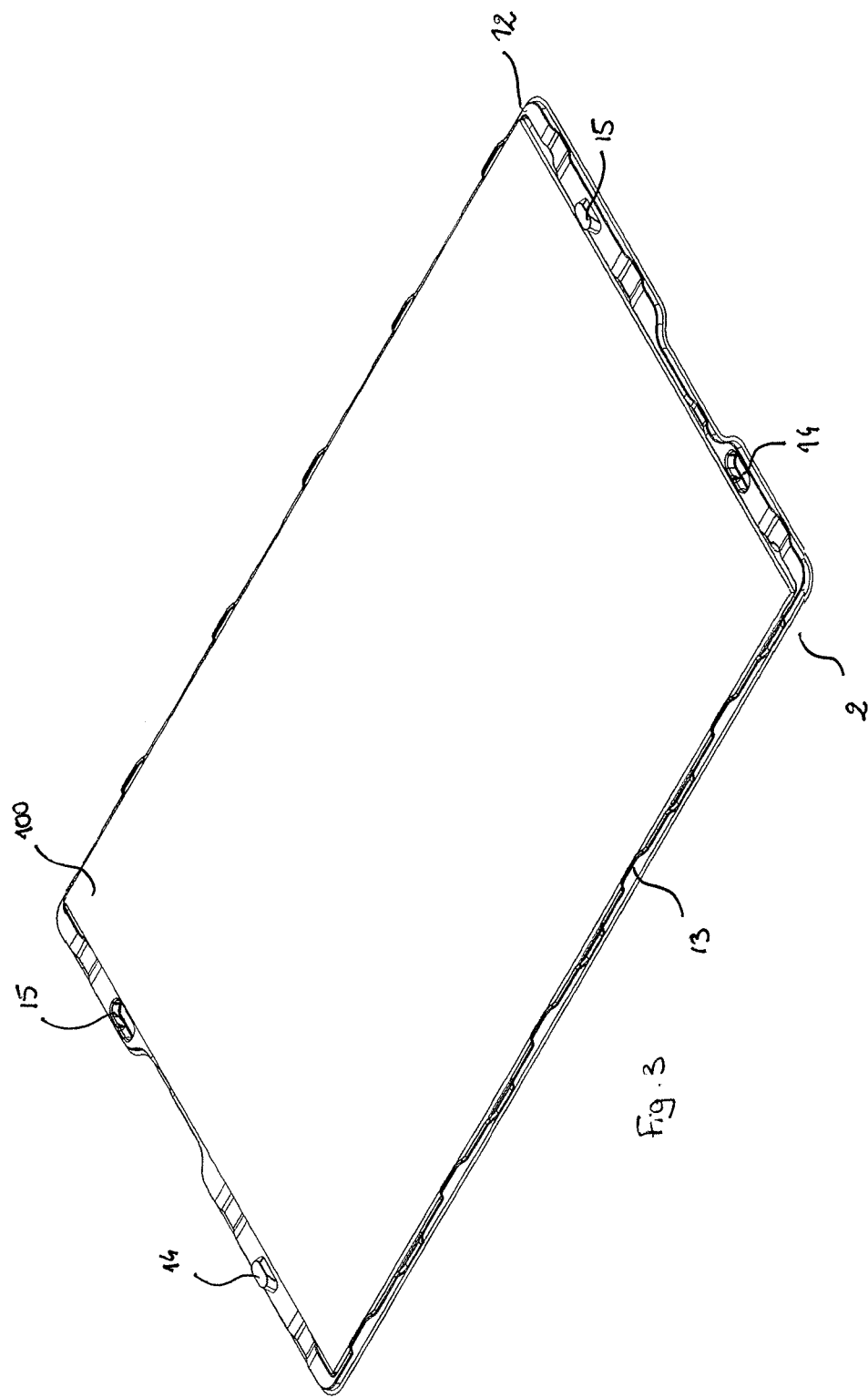
FIG. 3 includes a perspective view a the receiving member with a surgical mesh.

The surgical mesh 100 can be seen in FIG. 1 or 3.

The receiving member 2 has a generally planar shape. In the illustrated embodiment, the receiving member 2 comprises a series of resting ribs 4 protruding from an inner panel 5.

As depicted on FIG. 2, the receiving member 2 is thus provided with transverse ribs 4 and longitudinal ribs 4 which divide the inner panel 5 into diffusing compartments 8 as will be explained later.

Figure 2:
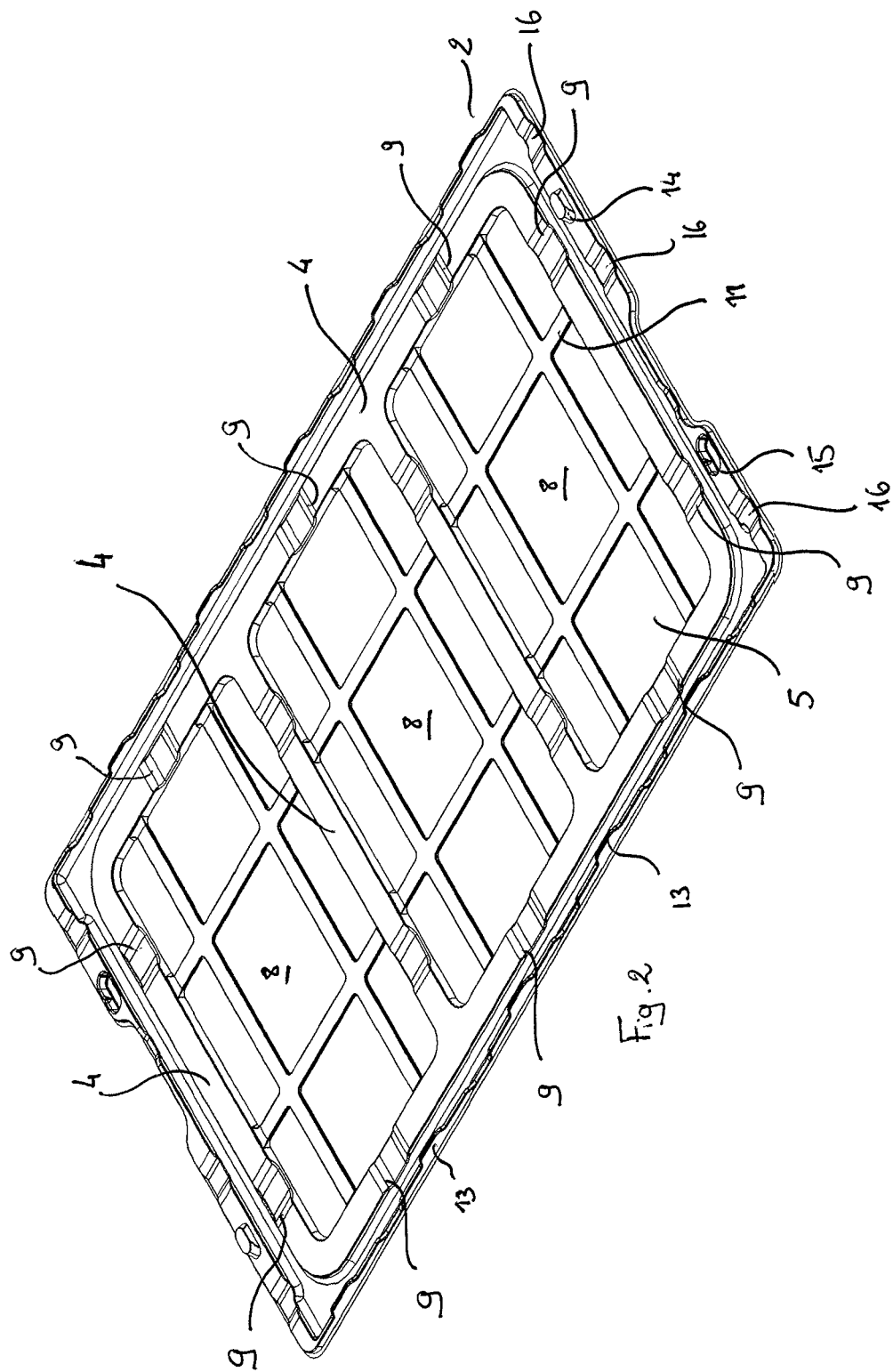
FIG. 2 includes a perspective view of a receiving member of the embodiment of FIG. 1.

In the embodiment of FIGS. 1 and 2, the receiving member 2 is provided with four transverse resting ribs 4 and two longitudinal resting ribs 4, which define three diffusing compartments 8.

The resting ribs 4 include at least one groove 9. In the embodiment of FIGS. 1 to 3, the resting ribs 4 are provided with a series of grooves 9 spaced out at regular intervals.

In embodiments, the inner wall 5 can be provided with strengthening ribs 11.

The receiving member 2 further includes a peripheral rim 12.

Along each length of the receiving member 2, the peripheral rim 12 includes a series of locking toothing 13.

Along each width of the receiving member 2, the peripheral rim 12 is provided with a locking pin 14 and a locking opening 15. The peripheral rim 12 can also include one or more grooves 16.

Figure 4:
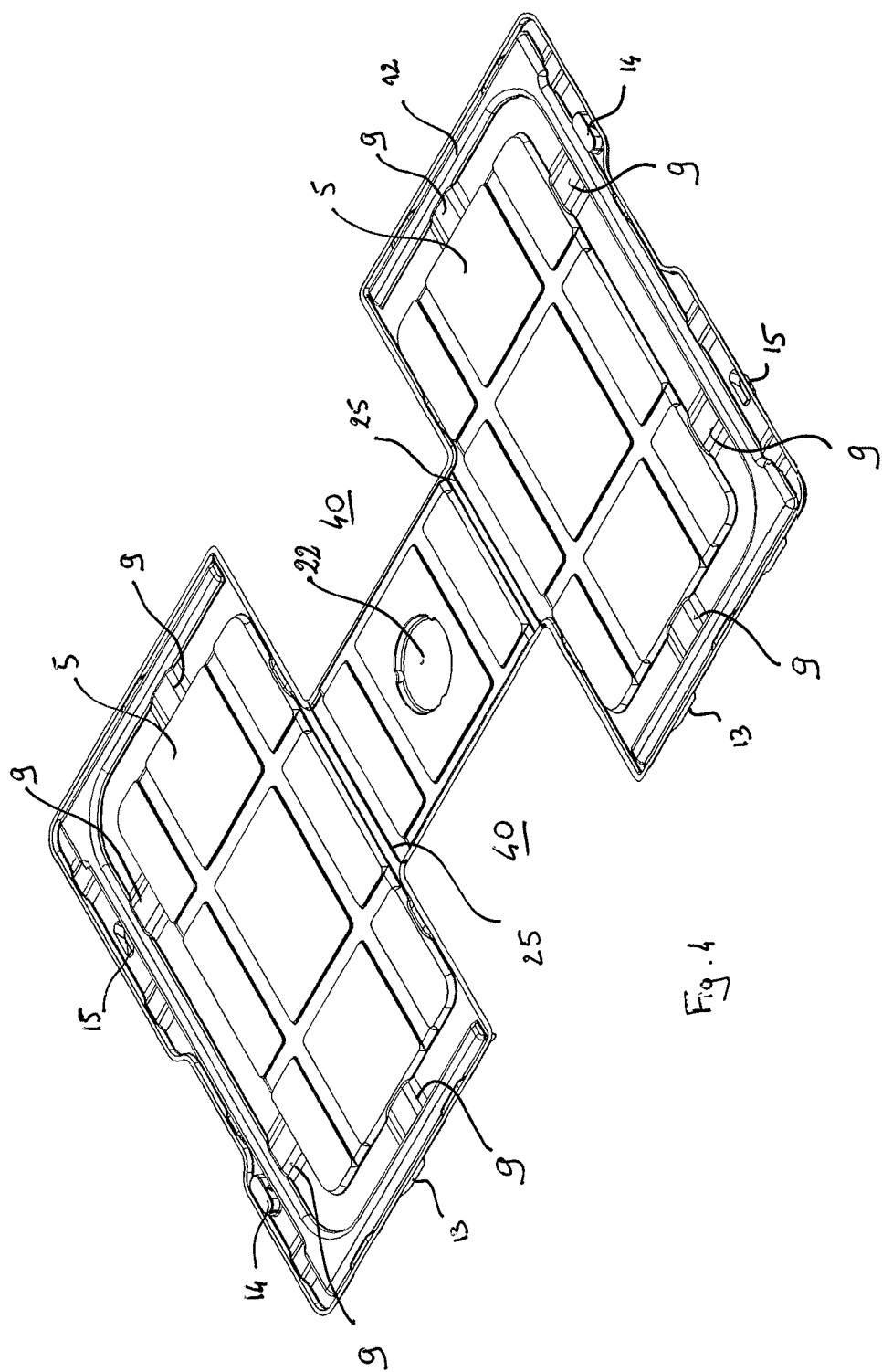
FIGS. 4 and 5 include perspective views of a covering member.
Figure 5:
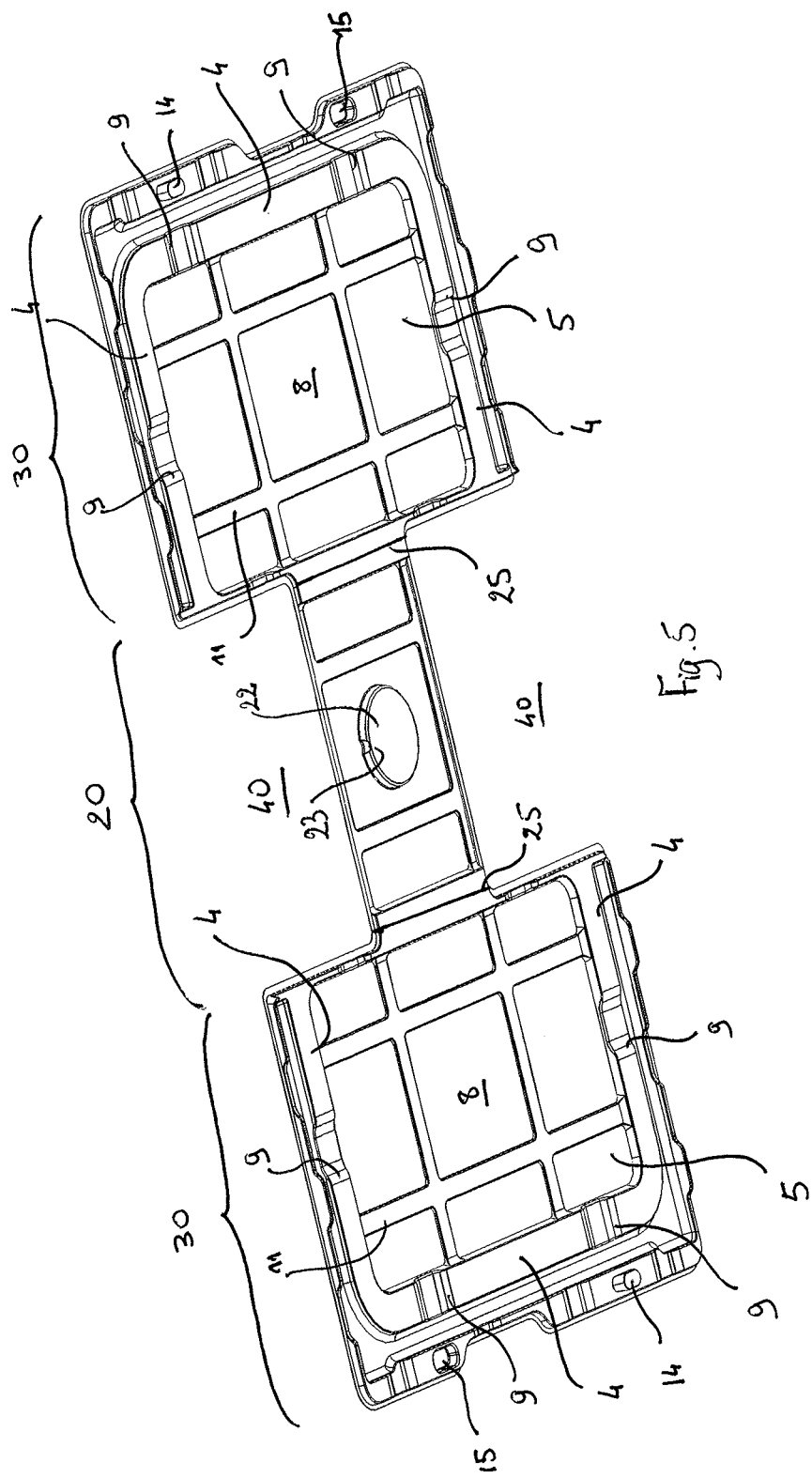

Turning to FIGS. 4 and 5, a covering member 3 is shown.

The covering member 3 has a generally planar shape. The covering member 3 has a substantially planar shape and is comprised of a central portion 20 and of two lateral portions 30 extending from the central portion 20 forming substantially a H. As can be seen on FIG. 4, the covering member 3 includes two symmetrical cut off portions 40.

In the illustrated embodiment, the covering member 3 comprises a series of resting ribs 4 protruding from an inner panel 5.

As depicted on FIG. 5, the covering member 3 is thus provided with transverse ribs 4 and longitudinal ribs 4, which define with the inner panel 5 diffusing compartments 8.

In the embodiment of FIGS. 4 and 5, the covering member 3 is provided with two transverse resting ribs 4 and two longitudinal resting ribs 4, which define a diffusing compartment 8 in each lateral portion 30.

The resting ribs 4 include at least one groove 9. In the embodiment of FIGS. 4 and 5, the resting ribs 4 are provided with a series of grooves 9 spaced out at regular intervals.

In embodiments, the inner wall 5 can be provided with strengthening ribs 11.

The covering member 3 further includes a peripheral rim 12.

Along each length of the covering member 3, the peripheral rim 12 includes a series of locking toothing 13.

Along each width of the receiving member 3, the peripheral rim 12 is provided with a locking pin 14 and a locking opening 15. The peripheral rim 12 can also include one or more grooves 16.

The central portion 20 can include a cavity 22 provided with three retaining tabs 23.

In an embodiment, the covering member 3 includes two weakened line 25 to form a hinge at the junction of the central portion 20 with each of the lateral portions 30.

The surgical mesh 100 is placed onto the receiving member 2 as can be seen on FIG. 3. The surgical mesh 100 seats on the resting ribs 4 and is surrounded by the peripheral rib 12.

The covering member 3 is placed above the receiving member 4 and is locked onto the receiving member 2. The locking pins 14 of the covering member 3 are engaged into the corresponding openings 15 of the receiving member 2. The locking toothing 13 of the receiving member 2 engage into the locking toothing of the covering member 3.

The surgical mesh 100 is thus interposed between the receiving member 2 and the covering member 3 and is maintained in a substantially flat position. The surgical mesh 100 is maintained between the resting ribs 4 of the receiving member 2 and the resting ribs 4 of the covering member 3.

It can be noted that, within the package 1, the gap between the resting ribs 4 of the receiving member 2 and the resting ribs 4 of the covering member 3 can be in the area of 1 mm while the surgical mesh 100 thickness can be in the area of 0.6 mm.

When positioned in the package 1, the surgical mesh 100 is thus maintained along the resting ribs 4; the part of the surgical mesh 100 which is not directly interposed between the resting ribs 4 of the receiving member 2 and of the covering member is received in the diffusing compartments 8 where the surgical mesh 100 is free from contact with the package.

The surgical mesh 100 positioned in the package 1 may then be sterilized by immersion in a sterilizing solution of gas including ethylene oxide.

The sterilizing gas can flow within the package 1 and diffuses into the surgical mesh 100 through the cut off portion 40 and through the grooves 9 provided in the resting ribs 4. The entire surface of the surgical mesh 100 is thus exposed to the sterilizing gas.

After sterilization, the package 1 can be hermetically sealed in a suitable envelope like container (not shown) to be stored for a later use.

The central cavity 22 can receive a capsule of a desiccant material to ensure that the any moisture within the surgical mesh 100 is captured. The desiccant capsule is maintained in position by the tabs 23. The cut off portions 40 provide a significant exposure to the action of the desiccant capsule.

It can be appreciated that the receiving portion 2 and the covering member 3 are devoid of sharp angles or sharp edges thus limiting the risk of damaging the container.

When needed on an operating room, the package 1 can be presented to the medical staff.

One of the lateral portions 30 of the covering member 3 may be lifted and may be folded along the weakened line 25 thereby giving access to the surgical mesh 100.

Figure 6:
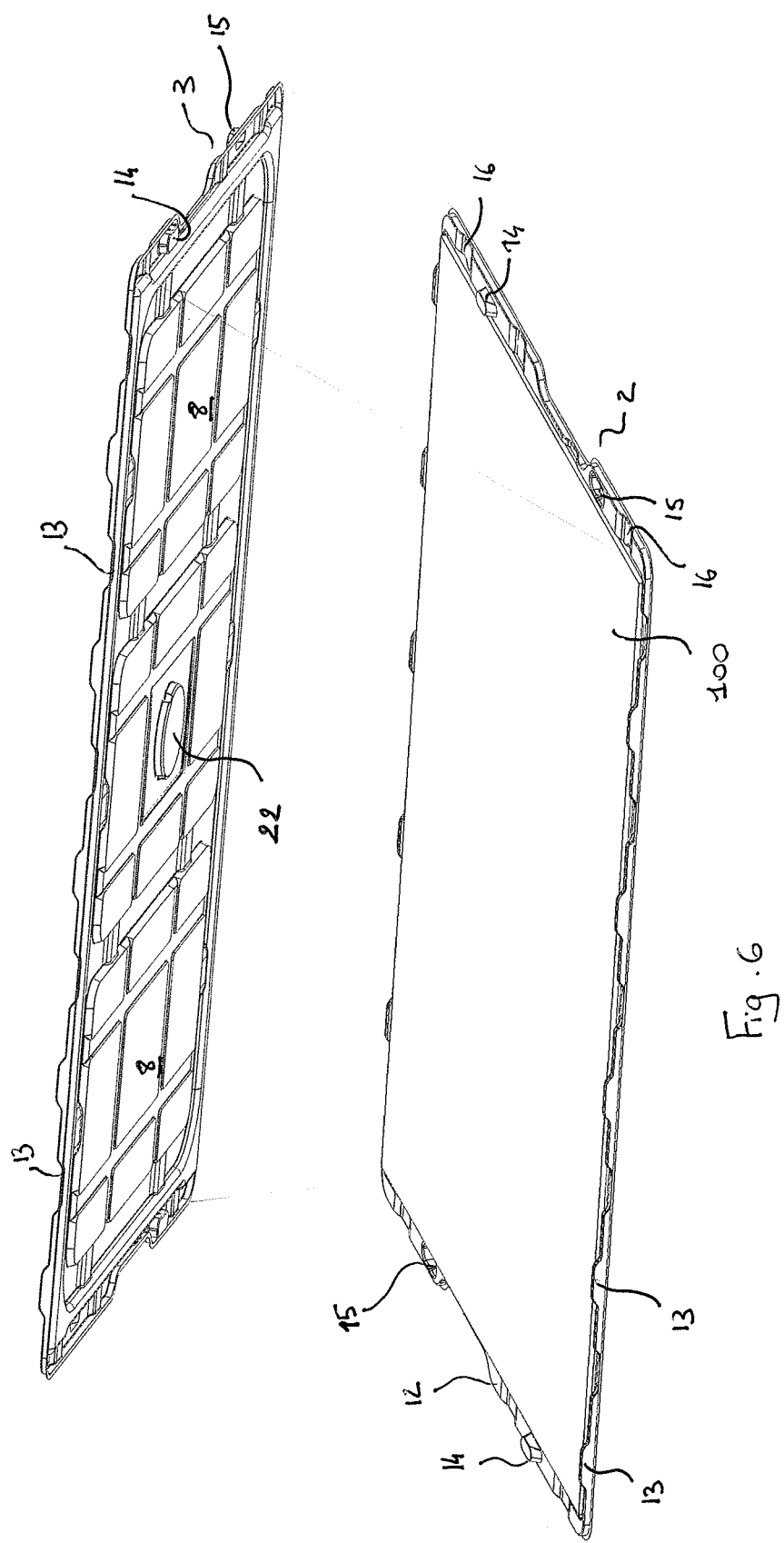
FIG. 6 includes an exploded view of another embodiment of the invention.

FIG. 6 depicts another embodiment of the invention.

In this embodiment of the invention, the receiving member 2 and the covering member 3 are identical.

A surgical mesh 100 is positioned onto a receiving member 2 such as the receiving member 2 illustrated on FIG. 2 and a covering member 3. The covering member 3 is structurally identical to the receiving member 2. However, the covering member 3 further includes a cavity 22 for a desiccant capsule.

The package described herein may be made of any material suitable for sterilization such as plastic, foils, combination thereof and laminates thereof and may be formed using any suitable molding process.

The invention claimed is:

1. A package for a surgical mesh comprising
a receiving member configured and dimensioned to receive at least one surgical mesh, the receiving member including transverse resting ribs and longitudinal resting ribs protruding from an inner wall of the receiving member and dividing the inner wall of the receiving member into diffusing compartments, the receiving member further comprising at least one first groove,
a covering member configured and dimensioned to cover the said at least one surgical mesh maintaining with the receiving member the at least one surgical mesh in a substantially flat position, the covering member comprising at least one second groove defining with the at least one first groove of the receiving member at least one channel configured for a sterilizing gas to flow within the at least one surgical mesh.

2. The package according to claim 1, wherein the receiving member and the covering member define at least one gas diffusing compartment connected to the at least one channel.

3. The package according to claim 1, wherein the covering member includes at least one cut off portion.

4. The package according to claim 2, wherein the covering member comprises at least one resting rib and an inner wall configured to maintain the surgical mesh between the resting ribs and to define the at least one gas diffusing compartment for a sterilizing gas.

5. The package according to claim 3, wherein the covering member comprises at least one transverse resting rib forming at least two diffusing compartments.

6. The package according to claim 1, wherein the receiving member and the covering member include a peripheral rim provided with at least one locking pin and at least one corresponding locking opening.

7. The package according to claim 6, wherein the peripheral rim includes a series of locking toothing.

8. The package according to claim 1, wherein at least one of the receiving member and of the covering member includes a cavity configured to receive a capsule of desiccant material.

9. The package according to claim 1, wherein the receiving member and the covering member have a substantially rectangular shape.

10. The package according to claim 1, wherein the covering member includes at least two cut off portions.

11. The package according to claim 1, wherein the covering member includes a central portion and two lateral portions extending from the central portion.

12. The package according to claim 1, wherein the covering member includes at least one hinge allowing access to the at least one surgical mesh.

13. The package according to claim 12, wherein the at least one hinge is formed by a weakened line.

14. The package according to claim 11, wherein at least one hinge is positioned at a junction of the central portion and the lateral portion.

15. The package according to claim 1, wherein the inner wall of the receiving member further includes strengthening ribs.

16. The package according to claim 1, wherein the covering member comprises transverse resting ribs and longitudinal resting ribs protruding from an inner wall of the covering member and dividing the inner wall of the covering member into diffusing compartments.

17. The package according to claim 16, wherein the inner wall of the covering member further includes strengthening ribs.

18. The package according to claim 8, wherein the cavity further comprises retaining tabs which maintain the capsule of desiccant material within the cavity.

* * * * *